United States Patent [19]

Kagano et al.

[11] Patent Number: 5,744,609
[45] Date of Patent: Apr. 28, 1998

[54] METHOD FOR PRODUCING ALKYLSULFINYLBENZAMIDES AND 1-2 BENZISOTHIAZOL-3-ONES

[75] Inventors: Hirokazu Kagano; Hiroshi Goda; Shigeki Sakaue, all of Kako-gun, Japan

[73] Assignees: Sumitomo Seika Chemicals Co., Ltd., Hyogo; Sumitomo Chemical Co., Ltd., Osaka, both of Japan

[21] Appl. No.: 831,533

[22] Filed: Apr. 7, 1997

Related U.S. Application Data

[62] Division of Ser. No. 581,109, Dec. 29, 1995, Pat. No. 5,672,751, which is a division of Ser. No. 342,038, Nov. 17, 1994, Pat. No. 5,508,416.

[30] Foreign Application Priority Data

Nov. 24, 1993 [JP] Japan ........................ 5-319179
Dec. 29, 1993 [JP] Japan ........................ 5-350932

[51] Int. Cl.$^6$ ........................ C07D 275/04; C07C 323/04
[52] U.S. Cl. ........................ 548/209; 564/162
[58] Field of Search ........................ 548/209; 564/162

[56] References Cited

U.S. PATENT DOCUMENTS

| 3,300,378 | 1/1967 | Fischer et al. ........................ 548/209 |
| 4,851,541 | 7/1989 | Maignan et al. ........................ 548/209 |

FOREIGN PATENT DOCUMENTS

| 3500577 | 7/1986 | Germany. |
| 9420479 | 9/1994 | WIPO. |

OTHER PUBLICATIONS

Y. Uchida et al., Bull. Chem. Soc. Jpn., 55:1183–87 (1982).
S. Wright et al., Tetrahedron (eh. 33(2):153–6 (1992).
Y. Uchida et al., Gazzetta Chimica Italiana 117:649–54 (1987).
J.A. Cipollina et al., J. Med. Chem. 34(11):3316–28 (1991).
Grivas, J. Org. Chem. 40:2029–32 (1975).
Bamfield et al., J. Chem. Soc. Perkin Trans. II, 691–696 (1988).
Kato et al., J. Med. Chem., 33(5):1406–13 (1990).
Uchida et al., Bull. Chem. Soc. Jpn., 54:1781–86 (1981).
Decicco et al., Tetrahedron Lett., 34(51):8213–16 (1993).

*Primary Examiner*—Johann Richter
*Assistant Examiner*—Laura Cross Lutz
*Attorney, Agent, or Firm*—Birch, Stewart, Kolasch & Birch, LLP

[57] ABSTRACT

A method for producing an alkylthiobenzamide by carrying out a reaction of a halobenzamide with an alkanethiol in the presence of a base in a heterogeneous solvent; a method for producing an alkylsulfinylbenzamide by carrying out a reaction of an alkylthiobenzamide with a halogen in a heterogeneous solvent; a method for producing an alkylsulfinylbenzamide by carrying out a reaction of a halobenzamide with an alkanethiol in the presence of a base in a heterogeneous solvent and a subsequent reaction with a halogen; and a method for producing a 1,2-benzisothiazol-3-one by carrying out a reaction of a 2-(alkylthio)benzamide with a halogenating agent.

5 Claims, No Drawings

METHOD FOR PRODUCING ALKYLSULFINYLBENZAMIDES AND 1-2 BENZISOTHIAZOL-3-ONES

This application is a divisional of application Ser. No. 08/581,109, filed on Dec. 29, 1955 now U.S. Pat. No. 5,672,751, which is a divisional of application Ser. No. 08/342,038 filed Nov. 17, 1994, now U.S. Pat. No. 5,508,416 the entire contents of which are hereby incorporated by reference.

BACKGROUND OF THE INVENTION

1. Field of the Invention

The present invention relates to a method for producing alkylsulfinylbenzamides and 1,2-benzisothiazol-3-ones. More particularly, the present invention relates to a method for producing alkylsulfinylbenzamides which are useful as intermediates for 1,2-benzisothiazol-3-ones, etc. and a method for producing 1,2-benzisothiazol-3-ones directly from 2-(alkylthio)benzamides. 1,2-benzisothiazol-3-ones are compounds useful as antibacterial agents and antifungal agents.

2. Discussion of the Related Art

The following methods are known for producing alkylsulfinylbenzamides.

(A) Bull. Chem. Soc. Jpn., 55, 1183–1187 (1982)

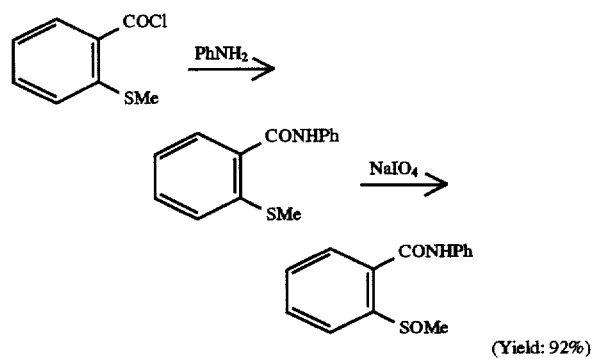

(Yield: 92%)

(B) Tetrahedron Lett., 33, 153–156 (1992)

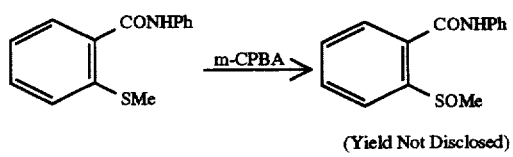

(Yield Not Disclosed)

These conventional methods, however, are not advantageous for industrial use for various reasons. Specifically, Method (A) has problems in stability and production of its starting material, 2-(methylthio)benzoyl chloride. Also, periodic acid, which is expensive and dangerous, is used in this method.

Method (B) has a problem in obtaining the starting material, because no methods have been disclosed for producing the starting material, N-phenyl-2-(methylthio) benzamide. In addition, this method also uses a dangerous substance, m-chloroperbenzoic acid (m-CPBA).

There are also several methods known for producing 1,2-benzisothiazol-3-ones, including the following ones.

(C) Bull. Chem. Soc. Jpn., 55, 1183–1187 (1982)

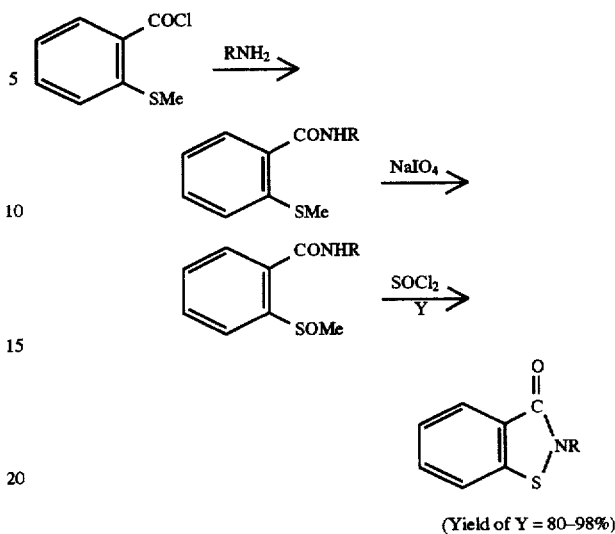

(Yield of Y = 80–98%)

In the above method, 2-(methylthio)benzamide is produced from 2-(methylthio)benzoylchloride; oxidized with periodic acid to 2-(methylsulfinyl)benzamide; and cyclized in the presence of thionyl chloride to yield a 1,2-benzisothiazol-3-one.

(D) Ger. Offen. 3500577 (1986)

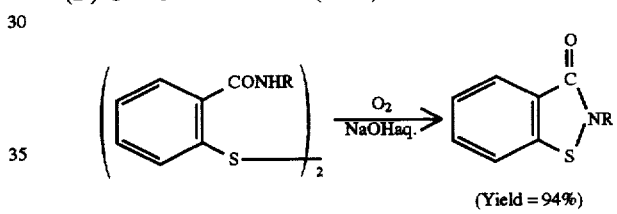

(Yield = 94%)

In the above method, a desired 1,2-benzisothiazol-3-one may be obtained using thiosalicylic acid as a starting material and sodium hydroxide as a cycling agent in the final process.

(E) J. Org. Chem. 40(14), 2029–2032 (1975)

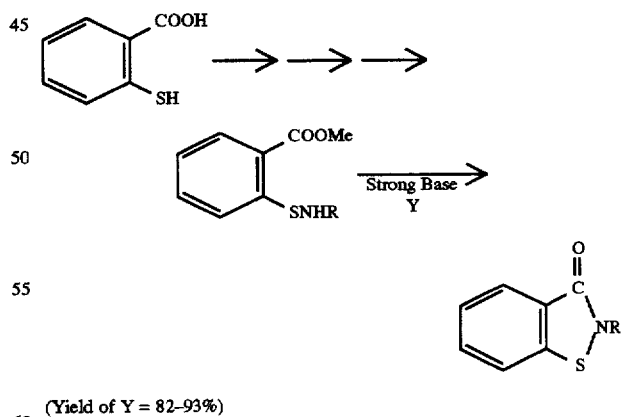

(Yield of Y = 82–93%)

In the above method, a desired 1,2-benzisothiazol-3-one is obtained using thiosalicylic acid as a starting material and a strong base in the final cyclization process.

However, these conventional methods have the following drawbacks:

In Method (C), a desired 1,2-benzisothiazol-3-one is synthesized in two steps, that is, 2-(methylthio)benzamide is oxidized to 2-(methylsulfinyl)benzamide, which is then cyclized in the presence of thionyl chloride. This method needs use of periodic acid, a dangerous and expensive substance.

Method (D) requires expensive thiosalicylic acid as the starting material, a strong base for cyclization, and involves many reaction steps. Therefore, this method is not satisfactory for industrial use.

Also, Method (E) uses expensive thiosalicylic acid as the starting material and a strong base for cyclization, and involves many reaction steps, and, therefore, is not suitable for industrial use.

As stated above, all known methods require more than one reaction steps to produce 1,2-benzisothiazol-3-ones from 2-(alkylthio)benzamides, and are not satisfactory for production on an industrial scale.

SUMMARY OF THE INVENTION

Accordingly, in view of the above problems, an object of the present invention is to provide a method for producing alkylsulfinylbenzamides industrially advantageously without using expensive and hazardous substances as the starting materials.

It is another object of the present invention to provide a method for producing alkylthiobenzamides which are useful as intermediates for the production of the alkylsulfinylbenzamides.

It is also an object of the present invention to provide a method for producing 1,2-benzisothiazol-3-ones, important compounds as antibacterial agents, antifungal agents, etc., in high yield, by a safe and short process without using any expensive and dangerous substances.

In order to achieve the above objects, the present inventors first investigated to provide an easy and economically advantageous method for producing alkylsulfinylbenzamides. As a result, the inventors found that an alkylsulfinylbenzamide represented by the general formula (IV) can easily be obtained in high yield by the reaction of a halobenzamide represented by general formula (I) with an alkanethiol represented by the general formula (II) in a heterogeneous solvent system in the presence of a base to yield an intermediary alkylthiobenzamide represented by the general formula (III), followed by a further reaction of this alkylthiobenzamide with a halogen in a heterogeneous solvent.

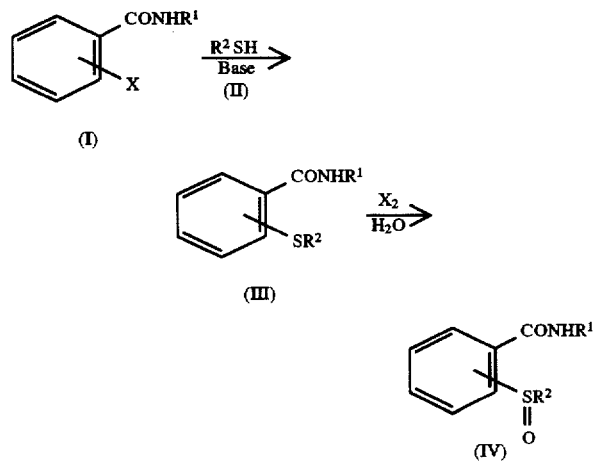

wherein X represents Cl or Br, R¹ represents a hydrogen atom, or an alkyl group having 1 to 4 carbon atoms, an aryl group, or an aralkyl group, and R² represents an alkyl group having 1 to 4 carbon atoms.

In order to achieve the object of the present invention, the inventors further investigated to develop an industrially advantageous method for producing 1,2-benzisothiazol-3-ones. As a result, the inventors unexpectedly found that a 1,2-benzisothiazol-3-one represented by the general formula (VI) can directly be obtained by a reaction between a 2-(alkylthio)benzamide represented by the general formula (V) and a halogenating agent. Unlike conventional methods, the cyclization can be achieved in one reaction step without via an intermediary alkylsulfinylbenzamide in this method.

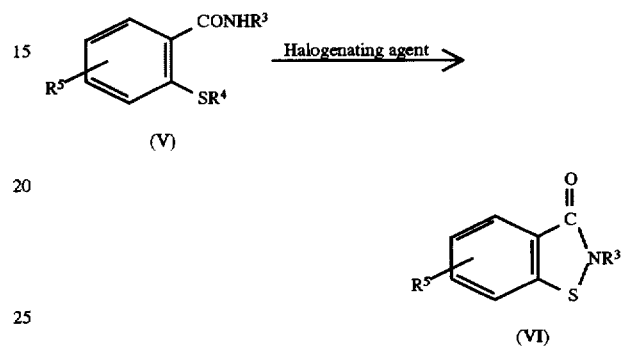

wherein R³ represents a hydrogen atom, or a linear or branched alkyl group having 1 to 12 carbon atoms, a cycloalkyl group, an aryl group, or an aralkyl group; R⁴ represents an alkyl group having 1 to 4 carbon atoms; R⁵ represents a hydrogen atom, an alkyl group having 1 to 4 carbon atoms, an alkoxy group having 1 to 4 carbon atoms, a nitro group, a carboxyl group or an ester thereof, or a halogen atom.

The present invention has been completed by conducting further research based upon the above findings.

The present invention is concerned with the following:

(1) A method for producing an alkylthiobenzamide represented by the general formula (III), comprising carrying out a reaction of a halobenzamide represented by the following general formula (I):

wherein X represents Cl or Br, and R¹ represents a hydrogen atom, or an alkyl group having 1 to 4 carbon atoms, an aryl group, or an aralkyl group, with an alkanethiol represented by the following general formula (II):

wherein R² represents an alkyl group having 1 to 4 carbon atoms, in the presence of a base in a heterogeneous solvent, to give an alkylthiobenzamide represented by the following general formula (III):

wherein R¹ and R² are defined as above;

(2) A method for producing an alkylsulfinylbenzamide represented by the following general formula (IV), comprising carrying out a reaction of an alkylthiobenzamide represented by the following general formula (III):

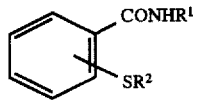

wherein $R^1$ and $R^2$ are defined as above, with a halogen in a heterogeneous solvent, to give an alkylsulfinylbenzamide represented by the following general formula (IV):

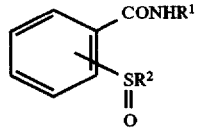

wherein $R^1$ and $R^2$ are defined as above;

(3) A method for producing an alkylsulfinylbenzamide represented by the general formula (IV), comprising carrying out a reaction of a halobenzamide represented by the following general formula (I):

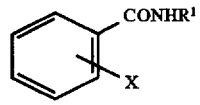

wherein X and $R^1$ are defined as above, with an alkanethiol represented by the following general formula (II):

$$R^2SH \quad (II)$$

wherein $R^2$ is defined as above, in the presence of a base in a heterogeneous solvent; and then adding a halogen to the above reaction mixture for a further reaction to give an alkylsulfinylbenzamide represented by the following general formula (IV):

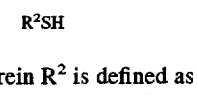

wherein $R^1$ and $R^2$ are defined as above; and (4) A method for producing a 1,2-benzisothiazol-3-one represented by the general formula (VI), comprising carrying out a reaction of a 2-(alkylthio)benzamide represented by the following general formula (V):

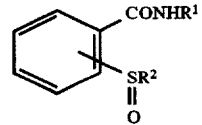

wherein $R^3$ represents a hydrogen atom, or a linear or branched alkyl group having 1 to 12 carbon atoms, a cycloalkyl group, an aryl group, or an aralkyl group; $R^4$ represents an alkyl group having 1 to 4 carbon atoms; $R^5$ represents a hydrogen atom, an alkyl group having 1 to 4 carbon atoms, an alkoxy group having 1 to 4 carbon atoms, a nitro group, a carboxyl group or an ester thereof, or a halogen atom, with a halogenating agent to give a 1,2-benzisothiazol-3-one represented by the following general formula (VI):

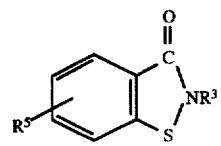

wherein $R^3$ and $R^5$ are defined as above.

According to the present invention, an alkylsulfinylbenzamide can readily be synthesized from a halobenzamide, the starting material easily available for industrial use, via an intermediary alkylthiobenzamide, in a one-pot process. The method of the present invention is industrially and economically advantageous because it allows to produce easily an alkylsulfinylbenzamide in high yield with less discharge of aqueous waste and without the use of expensive and hazardous substances.

Also, according to the present invention, 1,2-benzisothiazol-3-ones such as 2-phenyl-1,2-benzisothiazol-3-one and 1,2-benzisothiazol-3-one, important substances as antibacterial and antifungal agents, can be produced from alkylthiobenzamides in high yield in one-step and under safe reaction conditions without use of expensive and hazardous substances.

DETAILED DESCRIPTION OF THE INVENTION

The present invention will be explained in detail below by explaining methods for producing alkylsulfinylbenzamides and methods for producing 1,2-benzisothiazol-3-ones separately.

[A] Method for Producing Alkylsulfinylbenzamides

The method for producing alkylsulfinylbenzamides of the present invention is characterized in that a desired alkylsulfinylbenzamide can easily be produced in high yield under relatively mild conditions by novel reaction, wherein a halobenzamide, which is available at a low cost for industrial use, is converted to an intermediary alkylthiobenzamide.

1) Method for Producing Alkylthiobenzamides

The method for producing alkylthiobenzamides (III) of the present invention is a novel method characterized by a reaction of a halobenzamide represented by the general formula (I) with an alkanethiol represented by the general formula (II) in the presence of a base in a heterogeneous solvent system.

In the above general formulas (I), (II) and (III), $R^1$ represents a hydrogen atom, an alkyl group having 1 to 4 carbon atoms, an aryl group or an aralkyl group, and $R^2$ represents an alkyl group having 1 to 4 carbon atoms. The alkyl groups may be linear or branched. Examples of such alkyl groups include methyl, ethyl, n-propyl, isopropyl, n-butyl, isobutyl, sec-butyl and tert-butyl groups. Examples of the aryl groups include phenyl, 4-tolyl and 1-naphthyl groups. Examples of the aralkyl groups include benzyl and phenethyl groups.

The halobenzamides represented by the general formula (I) used in the present invention are not particularly limited, and examples thereof include 2-chlorobenzamide, N-ethyl-2-chlorobenzamide, N-phenyl-2-chlorobenzamide, N-4-tolyl-2-chlorobenzamide, N-benzyl-2-chlorobenzamide, 2-bromobenzamide, N-ethyl-2-bromobenzamide, N-phenyl-2-bromobenzamide, N-4-tolyl-2-bromobenzamide, N-benzyl-2-bromobenzamide, 4-chlorobenzamide, N-ethyl-4-chlorobenzamide, N-phenyl-4-chlorobenzamide, N-4- tolyl-4-chlorobenzamide, N-benzyl-4-chlorobenzamide, 4-bromobenzamide, N-ethyl-4-bromobenzamide, N-phenyl-4-bromobenzamide, N-4-tolyl-4-bromobenzamide, and N-benzyl-4-bromobenzamide.

Alkanethiols represented by the general formula (II) are exemplified by methanethiol, ethanethiol, 1-propanethiol, 1-butanethiol and 2-butanethiol. The amount of alkanethiol used is normally 0.8 to 3.0 times, preferably 1.0 to 2.0 times the molar quantity of halobenzamide used. If the amount of alkanethiol used is less than 0.8 times, unchanged halobenzamide increases. Even though the amount of alkanethiol exceeds 3.0 times, additional effect cannot be expected, and, therefore, it is economically disadvantageous.

Bases which can be used in the reaction of a halobenzamide with an alkanethiol include alkali metal hydroxides, such as sodium hydroxide and potassium hydroxide; alkali metal carbonates, such as sodium carbonate and potassium carbonate; and metal alcoholates, such as sodium methylate and sodium ethylate. From the economic viewpoint, sodium hydroxide is preferably used. The amount of base used is normally 0.8 to 3.5 times, preferably 1.0 to 2.5 times the molar quantity of halobenzamide used. If the amount of base used is less than 0.8 times, unchanged halobenzamide increases. Even if the amount of base used exceeds 3.5 times, additional effect cannot be expected, and, therefore, it is economically disadvantageous.

The method of the present invention for producing an alkylthiobenzamide represented by the general formula (III) is characterized in that the reaction is carried out in a heterogeneous solvent system in the presence of water. The reaction of the starting materials, a halobenzamide with an alkanethiol, is carried out in a two-phase solvent system, because a halobenzamide is insoluble in water. In these cases, a phase-transfer catalyst is preferably added to the reaction system to promote the reaction. Phase-transfer catalysts which can be used for this purpose include quaternary ammonium salts, such as benzyltriethylammonium bromide, benzyltrimethylammonium chloride, hexadecyltriethylammonium bromide, hexadecyltrimethylammonium chloride, dodecyltrimethylammonium chloride, octyltriethylammonium bromide, tetra-n-butylammonium bromide, tetra-n-butylammonium chloride, tetraethylammonium chloride and trioctylmethylammonium chloride; quaternary phosphonium salts, such as hexadecyltriethylphosphonium bromide, hexadecyltributylphosphonium chloride, tetra-n-butylphosphonium bromide, tetra-n-butylphosphonium chloride, trioctylethylphosphonium bromide and tetraphenylphosphonium bromide; and crown ethers, such as 18-crown-6, dibenzo-18-crown-6 and dicyclohexyl-18-crown-6. From the economic viewpoint, quaternary ammonium salts, such as tetra-n-butylammonium bromide and tetra-n-butylammonium chloride, are preferably used.

The amount of phase-transfer catalyst used is normally 0.005 to 0.5 times, preferably 0.01 to 0.2 times the weight of halobenzamide. When the amount of phase-transfer catalyst used is less than 0.005 times the weight of halobenzamide, adequate catalytic effect cannot be obtained. Even if the amount of phase-transfer catalyst used exceeds 0.5 times the weight of halobenzamide used, additional expected effect cannot be obtained, and, therefore, it is economically disadvantageous.

In order to facilitate the reaction and the separation of the reaction mixture, the reaction solvent used in the present invention is normally a heterogeneous solvent consisting of water and 1 to 10 parts by weight of a water-insoluble organic solvent based on 1 part by weight of water. Water-insoluble organic solvents are not particularly limited and include hydrocarbons, such as n-hexane, n-heptane, cyclohexane, methylcyclohexane, benzene, toluene and xylene; and halogenated hydrocarbons, such as methylene chloride, 1,2-dichloroethane and chlorobenzene. The amount of heterogeneous solvent used is normally 1 to 30 times the weight of halobenzamide.

The reaction temperature for the present invention is normally 0° to 150° C., preferably 20° to 120° C. Reaction temperature higher than 150° C. causes side reactions. On the other hand, the reaction rate unfavorably lowers to an impractical level when the reaction temperature is less than 0° C. The reaction time varies with the reaction temperature and the types of phase-transfer catalyst and reaction solvent and cannot be generalized, but it is normally in the range between 1 and 40 hours.

After completion of the reaction, an alkylthiobenzamide can be isolated and purified from the separated organic solvent layer by an ordinary procedure, such as crystallization. Since the water layer separated contains a phase-transfer catalyst, it can successively and repeatedly be used in subsequent reactions. Therefore, almost no aqueous waste is discharged out of the reaction system. The separated organic solvent layer containing an alkylthiobenzamide can also directly be used in the next reaction.

2) Method for Producing Alkylsulfinylbenzamides

An alkylsulfinylbenzamide represented by the general formula (IV) can be produced by the reaction of the thus-obtained alkylthiobenzamide represented by the general formula (III) with a halogen in a heterogeneous solvent system. $R^1$ and $R^2$ in the general formula (IV) have the same definitions as those of $R^1$ and $R^2$ in the general formula (III).

The halogens used here include chlorine and bromine. In view of the reaction selectivity, bromine is preferred. The amount of halogen is normally 0.8 to 2.0 times, preferably 1.0 to 1.3 times the molar quantity of alkylthiobenzamide. When the amount of halogen used is less than 0.8 times the molar quantity of alkylthiobenzamide, the amount of unchanged alkylthiobenzamide increases. On the other hand, the amount of halogen used exceeds 2.0 times, side reactions occur and lower the yield.

Hydrogen halides, by-products of the reaction between an alkylthiobenzamide and a halogen, can be neutralized in the reaction system. The bases used for this purpose include alkali metal hydroxides, such as sodium hydroxide and potassium hydroxide; alkali metal carbonates, such as sodium carbonate, potassium carbonate, sodium bicarbonate and potassium bicarbonate; metal alcoholates, such as sodium methylate and sodium ethylate; and organic amines, such as triethylamine and pyridine. From the economic viewpoint, sodium hydroxide or sodium bicarbonate is preferably used.

In order to facilitate the reaction and the isolation of the reaction product, the solvent used in the reaction between an alkylthiobenzamide and a halogen is normally a heterogeneous solvent system consisting of water and 1 to 10 parts by weight of a water-insoluble organic solvent based on 1 part by weight of water. Water-insoluble organic solvents are not particularly limited, and include hydrocarbons, such as n-hexane, n-heptane, cyclohexane, methylcyclohexane, benzene, toluene and xylene; and halogenated hydrocarbons, such as methylene chloride, 1,2-dichloroethane and chlorobenzene. The amount of heterogeneous solvent used is normally 1 to 30 times the weight of alkylthiobenzamide.

The reaction temperature for the reaction between an alkylthiobenzamide and a halogen is normally −10° to 100°

C., preferably 0° to 50° C. Reaction temperature higher than 100° C. causes side reactions. On the other hand, the reaction rate unfavorably lowers to an impractical level when the reaction temperature is less than −10° C. The reaction time varies with the reaction temperature and reaction solvent, and it is normally in the range between 1 and 40 hours.

In the present invention, starting with a halobenzamide represented by the general formula (I) and an alkanethiol having the general formula (II), an alkylthiobenzamide represented by the general formula (III) is first synthesized. This intermediary compound isolated is made to react with a halogen in the next step to yield a desired alkylsulfinylbenzamide. In the present invention, besides the above 2-step method, a one-pot reaction can also be used for producing alkylsulfinylbenzamides. In the one-pot redaction, a halobenzamide, an alkanethiol and a halogen are used as the starting materials. In this case, the organic solvent layer containing an intermediary alkylthiobenzamide is separated from the water layer by removal of the latter and made to react with a halogen without isolating the alkylthiobenzamide. When an alkylsulfinylbenzamide is to be obtained by the one-pot reaction, it is preferable to use a heterogeneous solvent system consisting of toluene and water. The isolation of alkylsulfinylbenzamide from the reaction mixture obtained by the two-step method or by the one-pot reaction can normally be carried out by crystallization or recrystallization from the separated organic solvent layer.

The thus-obtained alkylsulfinylbenzamide is represented by the general formula (IV). The alkylsulfinylbenzamides are exemplified by 2-(alkylsulfinyl)benzamides, such as 2-(methylsulfinyl)benzamide, 2-(ethylsulfinyl)benzamide, 2-(n-propylsulfinyl)benzamide, 2-(isopropylsulfinyl) benzamide, 2-(n-butylsulfinyl)benzamide, 2-(isobutylsulfinyl)benzamide, 2-(sec-butylsulfinyl) benzamide, 2-(tert-butylsulfinyl)benzamide, N-ethyl-2-(methylsulfinyl)benzamide, N-phenyl-2-(methylsulfinyl) benzamide, N-4-tolyl-2-(methylsulfinyl)benzamide, N-benzyl-2-(methylsulfinyl)benzamide, N-ethyl-2-(ethylsulfinyl)benzamide, N-phenyl-2-(ethylsulfinyl) benzamide, N-4-tolyl-2-(ethylsulfinyl)benzamide and N-benzyl-2-(ethylsulfinyl)benzamide, and 4-(alkylsulfinyl) benzamides, such as 4-(methylsulfinyl)benzamide, 4-(ethylsulfinyl)benzamide, N-ethyl-4-(methylsulfinyl) benzamide, N-phenyl-4-(methylsulfinyl)benzamide, N-4-tolyl-4-(methylsulfinyl)benzamide, and N-benzyl-4-(methylsulfinyl)benzamide.

[B] Method for Producing 1,2-benzisothiazol-3-ones

The method for producing a 1,2-benzisothiazol-3-one of the present invention is characterized in that a 2-(alkylthio) benzamide (V) is employed as the starting material readily available for industrial use, and cyclizes in only one step to directly produce a 1,2-benzisothiazol-3-one (VI), unlike conventional methods which involve two-step processes via an intermediary alkylsulfinylbenzamide. Another feature of this method lies in that a 1,2-benzisothiazol-3-one can be produced safely under relatively mild conditions without using dangerous and expensive substances.

The same definitions for $R^3$ and $R^5$ are applied to both the formulas (V) and (VI). Specifically, $R^3$ represents a hydrogen atom, a linear or branched alkyl group having 1 to 12 carbon atoms, a cycloalkyl group, an aryl group or an aralkyl group.

The alkyl groups for $R^3$ are exemplified by methyl, ethyl, n-propyl, isopropyl, n-butyl, isobutyl, sec-butyl, tert-butyl, n-pentyl, n-hexyl, n-heptyl, n-octyl, n-decyl and n-dodecyl groups. The cycloalkyl groups for $R^3$ are exemplified by cyclopentyl and cyclohexyl. The aryl groups for $R^3$ are exemplified by phenyl, 4-tolyl, 4-methoxyphenyl, 4-chlorophenyl and 1-naphthyl groups. The aralkyl group for $R^3$ is exemplified by benzyl and phenethyl.

Preferred examples of $R^3$ include a hydrogen atom, and methyl, ethyl, isopropyl, n-butyl, tert-butyl, n-dodecyl, cyclohexyl, phenyl, 4-tolyl, 4-methoxyphenyl, 4-chlorophenyl, 1-naphthyl and benzyl groups, with a greater preference given to a hydrogen atom and a phenyl group.

$R^4$ in the general formula (V) represents an alkyl group having 1 to 4 carbon atoms. The alkyl groups for $R^4$ are exemplified by methyl, ethyl, n-propyl, isopropyl, n-butyl, isobutyl, sec-butyl and tert-butyl groups.

Preferred examples of $R^4$ include methyl, ethyl, n-propyl and tert-butyl groups, with a greater preference given to methyl and tert-butyl groups.

$R^5$ in the general formulas (V) and (VI) represents a hydrogen atom, an alkyl group having 1 to 4 carbon atoms, an alkoxy group having 1 to 4 carbon atoms, a nitro group, a carboxyl group or ester thereof, or a halogen atom. The alkyl groups for $R^5$ are exemplified by methyl, ethyl, n-propyl, isopropyl, n-butyl, isobutyl, sec-butyl and tert-butyl groups. Alkoxy groups for $R^5$ are exemplified by methoxy, ethoxy, propoxy and butoxy groups. Esters of carboxyl group for $R^5$ are exemplified by methoxycarbonyl, ethoxycarbonyl, propoxycarbonyl and butoxycarbonyl. Halogens for $R^5$ are exemplified by chlorine and bromine.

Preferred examples for $R^5$ include a hydrogen atom, a n-butyl group, a methoxy group, a nitro group and a chlorine atom, with a greater preference given to a hydrogen atom.

The starting materials, 2-(alkylthio)benzamides represented by the general formula (V) in the present invention are not particularly limited, and examples thereof include the following: 2-(methylthio)benzamide, 2-(ethylthio) benzamide, 2-(tert-butylthio)benzamide, N-ethyl-2-(methylthio)benzamide, N-ethyl-2-(ethylthio)benzamide, N-isopropyl-2-(methylthio)benzamide, N-(tert-butyl)-2-(methylthio)benzamide, N-hexyl-2-(methylthio)benzamide, N-octyl-2-(methylthio)benzamide, N-decyl-2-(methylthio) benzamide, N-dodecyl-2-(methylthio)benzamide, N-cyclohexyl-2-(methylthio)benzamide, N-phenyl-2-(methylthio)benzamide, N-(4-tolyl)-2-(methylthio) benzamide, N-(4-methoxyphenyl)-2-(methylthio) benzamide, N-(4-chlorophenyl)-2-(methylthio)benzamide, N-(1-naphthyl)-2-(methylthio)benzamide, N-benzyl-2-(methylthio)benzamide, N-benzyl-2-(propylthio) benzamide, N-benzyl-2-(butylthio)benzamide, N-phenyl-3-methyl-2-(methylthio)benzamide, N-methyl-5-butyl-2-(methylthio)benzamide, N-butyl-4-methoxy-2-(methylthio) benzamide, N-phenyl-2-methylthio-3-nitrobenzamide, 4-chloro-2-(methylthio)benzamide, 4-carboxy-2-(methylthio)benzamide, and 4-methoxycarbonyl-2-(methylthio)benzamide.

Although a 2-(alkylthio)benzamide represented by the general formula (V) may be prepared by any methods, it can be obtained more advantageously by the aforementioned method for producing an alkylthiobenzamide of the present invention.

The method for producing a 1,2-benzisothiazol-3-one from a 2-(alkylthio)benzamide of the present invention is carried out by the reaction of the 2-(alkylthio)benzamide with a halogenating agent. The detail of this method is hereinafter described.

Any halogenating agents may be used for this process of the present invention, as long as it is capable of reacting with a sulfide to produce a sulfonium halide. Such reagents include sulfuryl halides [SO$_2$X$_2$ (VII), wherein X represents Cl or Br], such as sulfuryl chloride and sulfuryl bromide; phosphorus chlorides, such as phosphorus pentachloride and phosphorus triochloride; and such as chlorine, bromine and iodine. Among them, sulfuryl chloride, phosphorus pentachloride, phosphorus trichloride and chlorine are preferably used.

The reaction solvents used for the halogenation process to obtain 1,2-benzisothiazol-3-ones are not particularly limited as long as it is inert to the reaction. Examples of the reaction solvent include hydrocarbons, such as n-hexane, n-heptane, cyclohexane, methylcyclohexane, benzene, toluene and xylene; and halogenated hydrocarbons, such as methylene chloride, 1,2-dichloroethane, chloroform, carbon tetrachloride, and monochlorobenzene.

Of the above-mentioned reaction solvents, toluene, xylene and monochlorobenzene are preferred, because the entire process, i.e., from the synthesis of a 2-(alkylthio) benzamide represented by the general formula (V) by a reaction between a halobenzamide represented by the following general formula (VIII) and an alkanethiol represented by the following general formula (IX) to the synthesis of a 1,2-benzisothiazol-3-one by a reaction between the 2-(alkylthio)benzamide and a halogenating agent, can be very efficiently achieved in a one-pot:

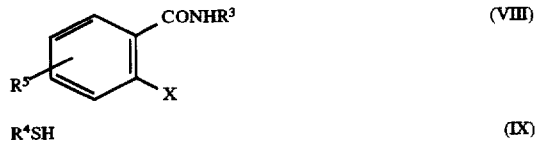

R$^4$SH                          (IX)

The conditions for the reaction between a halobenzamide (VIII) and an alkanethiol (IX) are the same as those for the reaction between a halobenzamide (I) and an alkanethiol (II).

The amount of solvent used is normally 1 to 30 times the weight of 2(alkylthio)benzamide used.

The reaction temperature is normally 0° to 150° C., preferably 20° to 120° C. Reaction temperature higher than 150° C. causes the problems of side reactions. On the other hand, reaction rate lowers to an impractical level when the reaction temperature is less than 0° C. The reaction time varies with the reaction temperature and the type of and reaction solvent, and it is normally in the range between 1 and 40 hours.

A desired 1,2-benzisothiazol-3-one can be isolated and purified from the thus-obtained reaction mixture by the conventional methods, i.e., by distillation under reduced pressure when the desired 1,2-benzisothiazol-3-one is liquid, or by direct crystallization or extraction and subsequent recrystallization when the desired 1,2-benzisothiazol-3-one is solid. There is no limitation to these method.

Examples of 1,2-benzisothiazol-3-ones represented by the general formula (VI) obtained by the method of the present invention include:

1,2-benzisothiazol-3-one, 2-ethyl-1,2-benzisothiazol-3-one, 2-isopropyl-1,2-benzisothiazol-3-one, 2-(tert-butyl)-1,2-benzisothiazol-3-one, 2-hexyl-1,2-benzisothiazol-3-one, 2-octyl-1,2-benzisothiazol-3-one, 2-decyl-1,2-benzisothiazol-3-one, 2-dodecyl-1,2-benzisothiazol-3-one, 2-cyclohexyl-1,2-benzisothiazol-3-one, 2-phenyl-1,2-benzisothiazol-3-one, 2-(4-tolyl)-1,2-benzisothiazol-3-one, 2-(4-methoxyphenyl)-1,2-benzisothiazol-3-one, 2-(4-chlorophenyl)-1,2-benzisothiazol-3-one, 2-(1-naphthyl)-1,2-benzisothiazol-3-one, 2-benzyl-1,2-benzisothiazol-3-one, 7-methyl-2-phenyl-1,2-benzisothiazol-3-one, 5-butyl-2-methyl-1,2-benzisothiazol-3-one, 2-butyl-6-methoxy-1,2-benzisothiazol-3-one, 7-nitro-2-phenyl-1,2-benzisothiazol-3-one, 6-chloro-1,2-benzisothiazol-3-one, 6-carboxy-1,2-benzisothiazol-3-one, and 6-methoxycarbonyl-1,2-benzisothiazol-3-one.

EXAMPLES

The present invention will be further described by means of the following working examples and a production example, without intending to restrict the scope of the present invention thereto.

Incidentally, the obtained product is confirmed by nuclear magnetic resonance method ($^1$H-NMR) and mass spectroscopy in order to determine whether a desired product is obtained.

Production Example 1

Production of N-Phenyl-2-chlorobenzamide

To a 500 ml four-necked flask equipped with a stirrer, a thermometer, and a condenser, 31.3 g (0.2 mol) of 2-chlorobenzoic acid and 180 g of toluene are placed. To the above mixture in the flask, 25.0 g (0.21 mol) of thionyl chloride is added dropwise over 30 minutes while stirring at a temperature of from 60° to 65° C. to be allowed to react with each other for about 30 minutes. To the above reaction mixture, a solution containing 27.9 g (0.3 mol) of aniline dissolved in 100 g of toluene is dropwise added to be allowed to react with each other at a temperature of from 70° to 75° C. for 30 minutes. After completion of the reaction, the reaction mixture is cooled to room temperature, and 70 g of a 5% by weight hydrochloric acid solution is added to the above mixture. The mixture is vigorously shaken and kept standing for separation of the toluene layer from the aqueous layer. After separation of the toluene layer, it is condensed to precipitate white crystals, followed by recrystallization (in a water/methanol mixture of 3/7), to give 43.1 g of N-phenyl-2-chlorobenzamide (melting point: 116° to 117° C.). The yield of the product against 2-chlorobenzoic acid is 93%.

Example 1

Production of N-Phenyl-2-(methylthio)benzamide

To a 500 ml four-necked flask equipped with a stirrer, a thermometer, and a condenser, 46.3 g (0.2 mol) of N-phenyl-2-chlorobenzamide obtained in Production Example 1, 100 g of toluene, and 9.3 g of an aqueous solution of 50% by weight tetra-n-butylammonium bromide are placed. Separately, 12.0 g (0.30 mol) of sodium hydroxide and 113.7 g of water are placed into another container under a nitrogen gas atmosphere, and 14.5 g (0.30 mol) of methanethiol are added to the above mixture at room temperature over about 1 hour to prepare 140.2 g of sodium salt solution of methanethiol. 140.2 g (0.3 mol) of the aqueous solution of sodium methyl mercaptan thus prepared is added to the mixture containing N-phenyl-2-chlorobenzamide described above at 80° C. while stirring, to be allowed to react with each other under reflux for 1 hour. After completion of the reaction, the reaction mixture is cooled to room temperature to precipitate white crystals, which are washed with water and then with toluene and dried, to give 46.2 g of N-phenyl-2-(methylthio)benzamide (melting point 148° to 149° C.). The yield of the product against N-phenyl-2-chlorobenzamide is 95%.

Example 2

Production of N-Phenyl-2-(methylsulfinyl) benzamide

To a 1000 ml four-necked flask equipped with a stirrer, a thermometer, and a condenser, 48.6 g (0.2 mol) of N-phenyl-2-(methylthio)benzamide obtained in Example 1, 300 g of toluene, and 200 g of a 10% by weight aqueous solution of potassium bicarbonate are placed. To the above mixture in the flask, 32.0 g (0.2 mol) of bromine is added dropwise while stirring at a temperature of from 10° to 15° C. to be allowed to react with each other for about 10 minutes. After completion of the reaction, the produced white crystals are filtered and then recrystallized from a mixture of water and ethanol (1:9) to give 48.7 g of N-phenyl-2-(methylsulfinyl)benzamide (melting point: 194° to 195° C.). The yield of the product against N-phenyl-2-(methylthio)benzamide is 94%.

Example 3

Production of N-Phenyl-2-(methylsulfinyl) benzamide from 2-Chlorobenzoic Acid by One-Pot Reaction To a 1000 ml four-necked flask equipped with a stirrer, a thermometer, and a condenser, 31.3 g (0.2 mol) of 2-chlorobenzoic acid and 300 g of toluene are placed, and the same procedures as in Production Example 1 are carried out. To the toluene layer containing the product, N-phenyl-2-chlorobenzamide, 9.3 g of an aqueous solution of 50% by weight tetra-n-butylammonium bromide is added. To this mixture, 140.2 g (0.3 mol) of an aqueous solution of sodium methyl mercaptan prepared as in Example 1 is added and the same reaction as in Example 1 is carried out. After completion of the reaction, the reaction mixture is separated while heating, and the toluene layer is separated out. To the obtained toluene layer, 200 g of a 10% by weight aqueous solution of potassium bicarbonate is added, and to this mixture, 38.4 g (0.24 mol) of bromine is added dropwise at a temperature of from 10° to 15° C. while stirring to be allowed to react with each other under the same conditions as in Example 2. As a result of conducting the entire procedure in one pot, the yield of N-phenyl-2-(methylsulfinyl)benzamide against 2-chlorobenzoic acid is 81%.

Example 4

Production of 2-Phenyl-1,2-benzisothiazol-3-one

To a 500 ml four-necked flask equipped with a stirrer, a thermometer, and a condenser, 48.6 g (0.2 mol) of N-phenyl-2-(methylthio)benzamide and 100 g of toluene are placed. To the above mixture in the flask, 29.7 g (0.22 mol) of sulfuryl chloride is added while stirring at a temperature of from 20° to 300° C., and then the components are heated and allowed to react with each other at a temperature of from 70° to 80° C. for 1 hour.

After completion of the reaction, the reaction mixture is cooled to room temperature, and the precipitated white crystals are washed with toluene, and then dried to give 44.0 g of 2-phenyl-1,2-benzisothiazol-3-one (melting point: 140° to 141° C.). The yield of the product is 97% against N-phenyl-2-(methylthio)benzamide, which is used as the starting material of the reaction.

Example 5

Production of 1,2-Benzisothiazol-3-one

To a 500 ml four-necked flask equipped with a stirrer, a thermometer, and a condenser, 33.4 g (0.2 mol) of 2-(methylthio)benzamide and 150 g of toluene are placed. To the above mixture in the flask, 28.3 g (0.21 mol) of sulfuryl chloride is added while stirring at a temperature of from 20° to 30° C., and then the components are heated and allowed to react with each other at a temperature of from 70° to 80° C. for 1 hour.

After completion of the reaction, the reaction mixture is cooled to room temperature, and the precipitated white crystals are washed with toluene, and then dried to give 29.0 g of 1,2-benzisothiazol-3-one (melting point: 157° to 158° C.). The yield of the product is 96% against 2-(methylthio)benzamide, which is used as the starting material of the reaction.

Examples 6 to 18

Production of 1,2-Benzisothiazol-3-ones

The same procedures as in Example 4 are carried out except that N-phenyl-2-(methylthio)benzamide is replaced with each of the 2-(alkylthio)benzamides shown in Tables 1 to 3, to give a corresponding 1,2-benzisothiazol-3-one. In the case where the corresponding 1,2-benzisothiazol-3-one is a liquid, it is obtained by distillation under a reduced pressure. The melting points and the yields of the products are also shown in Tables 1 to 3.

Example 19

Production of 2-Phenyl-1,2-benzisothiazol-3-one

The same procedures as in Example 4 are carried out except that sulfuryl chloride in Example 4 is replaced with 83.4 g (0.4 mol) of phosphorus pentachloride, to give 36.7 g of 2-phenyl-1,2-benzisothiazol-3-one. The yield of the product against N-phenyl-2-(methylthio)benzamide is 81%.

Example 20

Production of 2-Phenyl-1,2-benzisothiazol-3-one

To a 500 ml four-necked flask equipped with a stirrer, a thermometer, and a condenser, 48.6 g (0.2 mol) of N-phenyl-2-(methylthio)benzamide prepared as in Example 1 and 100 g of monochlorobenzene are placed. To the above mixture in the flask, 18.5 g (0.26 mol) of chlorine is added while stirring at a temperature of from 40° to 50° C., and then the components are heated and allowed to react with each other at a temperature of from 70° to 80° C. for 1 hour.

After completion of the reaction, the reaction mixture is cooled to room temperature, and the precipitated white crystals are washed with monochlorobenzene, and then dried to give 44.5 g of 2-phenyl-1,2-benzisothiazol-3-one (melting point: 140° to 141° C.). The yield of the product is 98% against N-phenyl-2-(methylthio)benzamide, which is used as the starting material of the reaction.

Example 21

Production of 1,2-Benzisothiazol-3-one

To a 500 ml four-necked flask equipped with a stirrer, a thermometer, and a condenser, 33.4 g (0.2 mol) of 2-(methylthio)benzamide and 150 g of monochlorobenzene are placed. To the above mixture in the flask, 18.5 g (0.26 mol) of chlorine is added while stirring at a temperature of from 40° to 50° C., and the components are then heated and allowed to react with each other at a temperature of from 70° to 80° C. for 1 hour.

After completion of the reaction, the reaction mixture is cooled to room temperature, and the precipitated white crystals are washed with monochlorobenzene, and then dried to give 29.3 g of 1,2-benzisothiazol-3-one (melting point: 157° to 158° C.). The yield of the product is 97% against 2-(methylthio)benzamide, which is used as the starting material of the reaction.

The results of Examples 4 to 21 are shown together in Tables 1 to 3.

TABLE 1

| Example No. | 2-(Alkylthio)benzamides | 1,2-Benzisothiazol-3-ones | Yield* (%) |
|---|---|---|---|
| 4 | N-Phenyl-2-(methylthio)benzamide | 2-Phenyl-1,2-benzisothiazol-3-one (melting point: 140–141° C.) | 97 |
| 5 | 2-(Methylthio)benzamide | 1,2-Benzisothiazol-3-one (melting point: 157–158° C.) | 96 |
| 6 | N-Ethyl-2-(ethylthio)benzamide | 2-Ethyl-1,2-benzisothiazol-3-one (boiling point: 126–127° C./2 mm Hg) | 94 |
| 7 | N-Isopropyl-2-(methylthio)benzamide | 2-Isopropyl-1,2-benzisothiazol-3-one (boiling point: 126–128° C./2 mmHg) | 92 |
| 8 | N-(tept-Butyl)-2-(methylthio)benzamide | 2-(tert-Butyl)-1,2-benzisothiazol-3-one (melting point: 57–58° C.) | 94 |
| 9 | N-Dodecyl-2-(methylthio)benzamide | 2-Dodecyl-1,2-benzisothiazol-3-one (a waxy solid) | 91 |

Note *: Yield of 1,2-Benzisothiazol-3-one against 2-(Alkylthio)benzamide.

TABLE 2

| Example No. | 2-(Alkylthio)benzamides | 1,2-Benzisothiazol-3-ones | Yield* (%) |
|---|---|---|---|
| 10 | N-Cyclohexyl-2-(methylthio)benzamide | 2-Cyclohexyl-1,2-benzisothiazol-3-one (melting point: 87–88° C.) | 93 |
| 11 | N-Benzyl-2-(propylthio)benzamide | 2-Benzyl-1,2-benzisothiazol-3-one (melting point: 87–88° C.) | 96 |
| 12 | N-(1-Naphthyl)-2-(methylthio)benzamide | 2-(1-Naphthyl)-1,2-benzisothiazol-3-one (melting point: 154–155° C.) | 94 |
| 13 | N-(4-Tolyl)-2-(methylthio)benzamide | 2-(4-Tolyl)-1,2-benzisothiazol-3-one (melting point: 136–137° C.) | 95 |
| 14 | N-(4-Methoxyphenyl)-2-(methylthio)-benzamide | 2-(4-Methoxyphenyl)-1,2-benzisothiazol-3-one (melting point: 148–149° C.) | 93 |
| 15 | N-Methyl-5-butyl-2-(methylthio)benzamide | 5-Butyl-2-methyl-1,2-benzisothiazol-3-one (melting point: 87–88° C.) | 92 |

Note *: Yield of 1,2-Benzisothiazol-3-one against 2-(Alkylthio)benzamide.

TABLE 3

| Example No. | 2-(Alkylthio)benzamides | 1,2-Benzisothiazol-3-ones | Yield* (%) |
|---|---|---|---|
| 16 | N-Butyl-4-methoxy-2-(methylthio)benzamide | 2-Butyl-6-methoxy-1,2-benzisothiazol-3-one (melting point: 50–51° C.) | 94 |
| 17 | N-Phenyl-2-methylthio-3-nitrobenzamide | 7-Nitro-2-phenyl-1,2-benzisothiazol-3-one (melting point: 152–153° C.) | 93 |
| 18 | 4-Chloro-2-(methylthio)benzamide | 6-Chloro-1,2-benzisothiazol-3-one (melting point: 271–272° C.) | 95 |
| 19 | N-Phenyl-2-(methylthio)benzamide | 2-Phenyl-1,2-benzisothiazol-3-one (melting point: 140–141° C.) | 81 |
| 20 | N-Phenyl-2-(methylthio)benzamide | 2-Phenyl-1,2-benzisothiazol-3-one (melting point: 140–141° C.) | 98 |
| 21 | 2-(Methylthio)benzamide | 1,2-Benzisothiazol-3-one (melting point: 157–158° C.) | 97 |

Note *: Yield of 1,2-Benzisothiazol-3-one against 2-(Alkylthio)benzamide.

What is claimed is:

1. A method for producing an alkylsulfinylbenzamide represented by the general formula (IV), comprising reacting an alkylthiobenzamide represented by the following general formula (III):

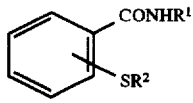

wherein $R^1$ represents a hydrogen atom, or an alkyl group having 1 to 4 carbon atoms, an aryl group, or an aralkyl group, and wherein $R^2$ represents an alkyl group having 1 to 4 carbon atoms, with a halogen in a heterogeneous solvent, to give an alkylsulfinylbenzamide represented by the following general formula (IV):

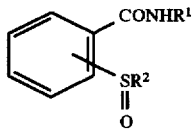

wherein $R^1$ and $R^2$ are defined as above.

2. The method according to claim 1, wherein the compound represented by the general formula (IV) is selected from the group consisting of 2-(methylsulfinyl)benzamide, 2-(ethylsulfinyl)benzamide, 2-(n-propylsulfinyl)benzamide, 2-(isopropylsulfinyl)benzamide, 2-(n-butylsulfinyl) benzamide, 2-(isobutylsulfinyl)benzamide, 2-(sec-butylsulfinyl)benzamide, 2-(tert-butylsulfinyl)benzamide, N-ethyl-2-(methylsulfinyl)benzamide, N-phenyl-2-(methylsulfinyl)benzamide, N-4-tolyl-2-(methylsulfinyl) benzamide, N-benzyl-2-(methylsulfonyl)benzamide, N-ethyl-2-(ethylsulfinyl)benzamide, N-phenyl-2-(ethylsulfinyl)benzamide, N-4-tolyl-2-(ethylsulfinyl) benzamide, N-benzyl-2-(ethylsulfinyl)benzamide, N-4-(methylsulfinyl)benzamide, 4-(ethylsulfinyl)benzamide, N-ethyl-4-(methylsulfinyl)benzamide, N-phenyl-4-(methylsulfinyl)benzamide, N-4-tolyl-4-(methylsulfinyl) benzamide, and N-benzyl-4-(methylsulfinyl)benzamide.

3. A method for producing an alkylsulfinylbenzamide represented by the general formula (IV), comprising reacting a halobenzamide represented by the following general formula (I):

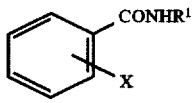

wherein X represents Cl or Br, and $R^1$ represents a hydrogen atom, or an alkyl group having 1 to 4 carbon atoms, an aryl group, or an aralkyl group, with an alkanethiol represented by the following general formula (II):

wherein $R^2$ represents an alkyl group having 1 to 4 carbon atoms, in the presence of a base in a heterogeneous solvent; then adding a halogen to the above reaction mixture for a further reaction to give an alkylsulfinylbenzamide represented by the following general formula (IV):

wherein $R^1$ and $R^2$ are defined as above.

4. The method according to claim 3, wherein the reaction is carried out in a one-pot process in a heterogeneous solvent consisting of toluene and water.

5. A method for producing a 1,2-benzisothiazol-3-one which comprises:

(1) reacting a halobenzamide represented by the following general formula (VIII):

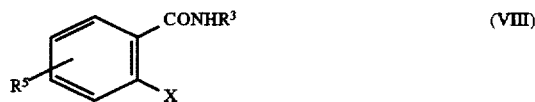

wherein X represents Cl or Br; $R^3$ represents a hydrogen atom, or a linear or branched alkyl group having 1 to 12 carbon atoms, a cycloalkyl group, an aryl group, or an aralkyl group; and $R^5$ represents a hydrogen atom, an alkyl group having 1 to 4 carbon atoms, an alkoxy group having 1 to 4 carbon atoms, a nitro group, a carboxyl group or an ester thereof, or a halogen atom, with an alkanethiol represented by the following general formula (IX):

wherein $R^4$ represents an alkyl group having 1 to 4 carbon atoms, in .the presence of a base in a heterogeneous solvent, to produce 2-(alkylthio)benzamide represented by the formula (V):

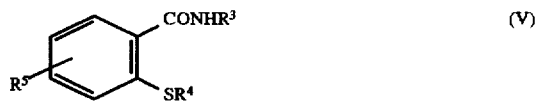

wherein $R^3$, $R^4$, and $R^5$ are defined as above; and (2) reacting said 2-(alkylthio)benzamide of formula (V) with a halogenating agent to give a 1,2-benzisothiazol-3-one represented by the following general formula (VI):

wherein $R^3$ and $R^5$ are defined as above.

* * * * *